US009687837B1

(12) United States Patent
Devon

(10) Patent No.: US 9,687,837 B1
(45) Date of Patent: Jun. 27, 2017

(54) STABLE HYDROFORMYLATION CATALYST FOR PREPARATION OF HIGH N/ISO RATIO ALDEHYDE PRODUCT

(71) Applicant: Eastman Chemical Company, Kingsport, TN (US)

(72) Inventor: Thomas James Devon, Longview, TX (US)

(73) Assignee: Eastman Chemical Company, Kingsport, TN (US)

( * ) Notice: Subject to any disclaimer, the term of this patent is extended or adjusted under 35 U.S.C. 154(b) by 0 days.

(21) Appl. No.: 15/253,342

(22) Filed: Aug. 31, 2016

(51) Int. Cl.
| C07C 45/50 | (2006.01) |
| B01J 31/00 | (2006.01) |
| C07F 9/00 | (2006.01) |
| B01J 31/24 | (2006.01) |
| C07F 9/50 | (2006.01) |

(52) U.S. Cl.
CPC ......... B01J 31/2409 (2013.01); C07C 45/505 (2013.01); C07F 9/5031 (2013.01); B01J 2231/321 (2013.01); B01J 2531/822 (2013.01)

(58) Field of Classification Search
CPC .................. C07C 45/50; B01J 31/2409; B01J 2231/3321; C07F 9/5031
USPC ........................................................ 568/454
See application file for complete search history.

(56) References Cited

U.S. PATENT DOCUMENTS

| 3,527,809 | A | 9/1970 | Pruett |
| 4,193,943 | A | 3/1980 | Unruh |
| 4,201,714 | A | 5/1980 | Hughes |
| 4,247,486 | A | 1/1981 | Brewester |
| 4,277,627 | A | 7/1981 | Bryant |
| 4,694,109 | A | 9/1987 | Devon et al. |
| 4,755,624 | A | 7/1988 | Phillips et al. |
| 4,760,194 | A | 7/1988 | Phillips et al. |
| 4,774,362 | A | 9/1988 | Devon et al. |
| 4,824,977 | A | 4/1989 | Devon et al. |
| 4,885,401 | A | 12/1989 | Billig et al. |
| 4,912,271 | A | 3/1990 | Thelen et al. |
| 4,912,276 | A | 3/1990 | Puckette |
| 4,939,309 | A | 7/1990 | Puckette |
| 4,960,949 | A | 10/1990 | Devon et al. |
| 5,061,669 | A | 10/1991 | Puckette |
| 5,102,971 | A | 4/1992 | Himmler et al. |
| 5,332,846 | A | 7/1994 | Devon et al. |
| 5,364,950 | A | 11/1994 | Babin et al. |
| 5,602,228 | A | 2/1997 | Wang et al. |
| 5,789,624 | A | 8/1998 | Unruh et al. |
| 5,922,898 | A | 7/1999 | Miller |
| 5,929,289 | A | 7/1999 | Abatjoglou et al. |
| 6,566,572 | B2 | 5/2003 | Okamoto et al. |
| 7,709,659 | B2 | 5/2010 | Zhang |
| 2002/0077250 | A1 | 6/2002 | Eckert et al. |

FOREIGN PATENT DOCUMENTS

WO        WO 01/44147 A1    6/2001

OTHER PUBLICATIONS

Yu et al. Highly Regioselective Isomerization-Hydroformylation of Internal Olefins to Linear Aldehyde Using Rh Compexes with Tetraphosphorus Ligands. Organic Letters, 2008, vol. 10 (16), 3469-3472.*
Saikia et al. Synthesis of cationic rhodium(I) and iridium (I) carbonyl complexes of tetradentate P(CH2CH2PPh2)3 ligand: An implication of steric inhibition and catalytic hydroformylation reaction. Journal of Molecular Catalysis A: Chemical, 2014, vol. 381, 188-193.*
Acros Organics, "Grignard Reagents" brochure; retrieved on-line Aug. 30, 2016 from http://www.acros.com/myBrochure/AO_Brochure-Grignard.pdf.
Agranat, Israel, et al.; "Multiple Horner-Emmons Cyclizations as a Route to Nonbenzenoid Aromatics. Synthesis of Polycyclic Dodecalenes"; J. Org. Chem., vol. 44, No. 12; 1979; pp. 1936-1941.
Berthiol, Florian et al.; "Reaction of aryl di-, tri-, or tetrabromides with arylboronic acids or alkenes in the presence of a palladium-tetraphosphine catalyst"; Journal of Organometallic Chemistry, vol. 689; 2004; pp. 2786-2798.
Colon, Ismael and Kelsey, Donald R.; "Coupling of Aryl Chlorides by Nickel and Reducing Metals"; J. Org. Chem., vol. 51, No. 14; 1986; pp. 2627-2637.
Ikoma, Yoshibaru et al.; "Halogen Selectivity in Nickel Salt-Catalyzed Cross-Coupling of Aryl Grignard Reagents with Bromochlorobenzenes—A Novel Synthetic Method of Unsymmetrical Terphenyl"; Synthetic Communications, vol. 21, No. 3; 1991; pp. 481-487.
Kranenburg, Mirko et al.; "New Diphosphine Ligands Based on Heterocyclic Aromatics Inducing Very High Regioselectivity in Rhodium-Catalyzed Hydroformylation: Effect of the Bite Angle"; Organometallics, vol. 14; 1995; pp. 3081-3089.
Maigrot, Nicole and Mazaleyrat, Jean-Paul; "New and Improved Synthesis of Optically Pure (R)- and (S)-2,2'-Dimethyl-1,1'-binaphthyl and Related Compounds"; Synthesis Communications; Mar. 1985; pp. 317-320.
Suzuki, Akira; "Recent advances in the cross-coupling reactions of organoboron derivatives with organic electrophiles, 1995-1998"; Journal of Organometallic Chemistry, vol. 576; 1999; pp. 147-168.
Van Der Slot, Saskia, et al.; "Rhodium-Catalyzed Hydroformylation and Deuterioformylation with Pyrrolyl-Based Phosphorus Amidite Ligands: Influence of Electronic Ligand Properties"; Organometallics, vol. 21; 2002; pp. 3873-3883.
Yan, Yongjun, et al.; "Retaining Catalyst Performance at High Temperature: The Use of a Tetraphosphine Ligand in the Highly Regioselective Hydroformylation of Terminal Olefins"; Adv. Synth. Catal, vol. 349; 2007; pp. 1582-1586.

(Continued)

*Primary Examiner* — Sikarl Witherspoon
(74) *Attorney, Agent, or Firm* — James Arnold, Jr.

(57) ABSTRACT

A new stable, catalytically active, tetradentate organophosphorus modified rhodium hydroformylation catalyst has been discovered that is capable of producing aldehyde products with a high linear/branched product ratio from linear olefins. The tetradentate organophosphorus modifier is a tetrasubstituted 2,2',2",5'-tetramethyl-1,1':4'-1"-terphenyl, whereby, each methyl group has one hydrogen substituted by an R, R'-diorganophosphine moiety. The R, R' may comprise aromatic, alkyl, arylalkyl and alkylaryl groups. The precursor 2,2',2",5'-tetramethyl-1,1':4',1"-terphenyl hydrocarbon may be prepared from para-xylene and toluene derivatives.

19 Claims, No Drawings

(56) References Cited

OTHER PUBLICATIONS

Yan, Yongjun, et al.; "A Tetraphosphorus Ligand for Highly Regioselective Isomerization-Hydroformlation of Internal Olefins"; J. Am. Chem. Soc., vol. 128; 2006; pp. 16058-16061.
Copending U.S. Appl. No. 15/253,316 filed Aug. 31, 2016; Thomas James Devon.
Office Communication notification date Mar. 10, 2017 received in co-pending U.S. Appl. No. 15/253,316.
Copending U.S. Appl. No. 15/253,360 filed Aug. 31, 2016; Thomas James Devon.
Office Action notification date Feb. 27, 2017 received in U.S. Appl. No. 15/523,360.

\* cited by examiner

US 9,687,837 B1

STABLE HYDROFORMYLATION CATALYST FOR PREPARATION OF HIGH N/ISO RATIO ALDEHYDE PRODUCT

BACKGROUND

The hydroformylation reaction is of great commercial importance for the preparation of very large quantities of derivatives generally known by the term "oxo alcohols". In the hydroformylation of propylene, the ratio of linear n-butyraldehyde to co-product isobutyraldehyde (N/Iso ratio) products has great importance in the efficient use of propylene for preparation of n-butanol, 2-ethylhexanol and derivatives of these from the linear n-butyraldehyde product. There is a need to attain high N/Iso ratio product in many business cases. Likewise, if the hydroformylation of higher molecular weight linear alpha-olefins is carried out, there is a need to selectively prepare the linear isomer aldehyde product as opposed to the less valuable branched isomer.

The use of triarylphosphine modifier, or ligand, as a co-catalyst with rhodium was disclosed in U.S. Pat. Nos. 3,527,809 and 4,247,486. The preferred ligand was triphenylphosphine. The patent art indicated that butyraldehyde N/Iso ratios of 8/1 to 12/1 were achievable when large quantities of ligand were used, typically up to 10% by weight in the catalyst solution. Triphenylphosphine is known as a monodentate ligand, meaning that the ligand molecule has one phosphorus atom to coordinate with the rhodium catalyst. Further studies indicated that the rhodium catalyst is more selective for preparing high N/Iso ratios when a high concentration of triphenylphosphine is present, allowing two ligands to coordinate with the rhodium during the catalyst cycle. The use of high concentrations of monodentate ligand and reduced reactor temperatures were also discovered to allow the catalyst to be more stable for long operating times as disclosed in U.S. Pat. No. 4,277,627.

The design and use of bi-dentate ligands with rhodium has been particularly successful in developing new hydroformylation catalyst systems capable of preparing aldehyde products with high N/Iso ratios. The use of sterically hindered bis-phosphites of substituted 2,2'-biphenol in combination with rhodium prepare butyraldehyde with N/Iso ratios of 30/1 U.S. Pat. No. 4,885,401. Van Leeuwen et. al. (Organometallics 2002, 21, pp. 3873-3883) disclosed the use of a ligand, bis(dipyrrolylphosphoramidite) ester of 2,2'-biphenol, with rhodium that is highly selective for the preparation of linear aldehyde products from 1-hexene. These two bidentate ligands are characterized by having the phosphorus atom bound in sigma bonds to oxygen and or nitrogen heteroatoms. While being selective for making linear products, these classes of phosphorus compounds are prone to decomposition with time by acid catalyzed reactions with aldehyde and alcohol coproducts present in the reactor. In the case of the commercialized bis-phosphite catalyst system, many methods have been disclosed in the patent literature to mitigate against the natural course of this class of ligand to react with the products of the hydroformylation reaction as disclosed in U.S. Pat. Nos. 5,929,289 and 5,364,950.

Other bidentate ligands based on phosphorus being bound to three carbon atom linkages have been successful in the preparation of aldehyde product with differing degrees of N/Iso ratio selectivity. 1,1'-bis(diphenylphosphino)ferrocene ligand and substituted versions have been reported to prepare heptanal with 10/1 N/Iso ratios with rhodium as disclosed in U.S. Pat. Nos. 4,193,943 and 5,789,624. The bidentate ligand "DIOP" in combination with rhodium produced butyraldehyde in a N/iso ratio of about 4/1, U.S. Pat. No. 4,201,714. 1,2-bis(diphenylphosphinomethyl)benzene in combination with rhodium produced butyraldehyde in a 2.28/1 N/Iso ratio, in U.S. Pat. No. 4,960,949. A bidentate ligand, alpha, beta-bis(diphenylphosphino)-2-ethyltoluene in combination with rhodium produced butyraldehyde with a 5.9/1 N/Iso ratio, in U.S. Pat. No. 4,774,362.

Bidentate ligands based on 2,2'-bis(diphenylphosphinomethyl)-1,1'-biphenyl and derivatives thereof have been useful as catalyst ligands in combination with rhodium to produce active hydroformylation catalysts that produce butryraldehyde with N/Iso ratios in excess of 25/1. These are disclosed in U.S. Pat. Nos. 4,694,109, 4,755,624 and 4,760,194. Another bidentate ligand based on a derivative of 2,2'-bis(dibenzophospholylmethyl)-1,1'-biphenyl produced butyraldehyde N/Iso ratios in excess of 100/1, U.S. Pat. No. 5,332,846.

The diphosphorus bidentate ligands, generally known as triorganophosphine bidentates are based on phosphorus atoms being bound to three carbon atoms. They have an advantage of catalyst stability against chemical decomposition reactions brought about by reaction with aldehyde product and alcohol coproduct present in the hydroformylation reactor. In spite of this advantage, triorganophosphine ligand catalyst systems can undergo "intrinsic deactivation" during rhodium catalyzed hydroformylation, especially in the case when using triphenylphosphine ligand. This was disclosed in some detail in U.S. Pat. No. 4,277,627. The patent indicated that high ligand/Rh mole ratios and relatively low reaction temperatures stabilized the active catalyst during hydroformylation against intrinsic deactivation. Intrinsic deactivation manifests itself by the gradual darkening of recovered catalyst solution due to the formation of inactive compounds that incorporate multiple rhodium atoms bound by decomposition products of degraded triorganophosphine ligands. These dark materials are generally known as rhodium clusters. Thus a stable catalyst is observed to remain a typically light yellow color, while ligands less stable undergo a progressive darkening, through amber to orange to eventually dark amber and brown as these inactive materials accumulate in the catalyst.

X. Zhang disclosed the use of a "tetraphosphine" ligand, namely 2,2',6,6'-tetrakis(diphenylphosphinomethyl)-1,1'-biphenyl "Advances in Synthetic Catalysis" 2007, 349, pp. 1582-1586 that they assert is capable of producing nonanal or heptanal with a high linear/branched product ratios using 1-octene or 1-hexene respectively in combination with rhodium under hydroformylation conditions. They further demonstrate that having the tetradentate ligand of their definition permits the catalyst to produce linear/branched ratio product in higher ratios than the corresponding 2,2'-bis(diphenylphosphinomethyl)-1,1'-biphenyl ligand, BISBI, the catalyst of U.S. Pat. No. 4,694,109, at higher reaction temperatures. They assert in their article that having extra phosphorus bonding sites available on the ligand molecule helped to stabilize the catalyst to attain higher N/Iso ratio selectivity at higher temperature. While this constitutes an improvement in the art of hydroformylation, their ligand of record is relatively synthetically inaccessible if large quantities are required as would be the case in a commercial hydroformylation application.

The tetraphosphine of Zhang is prepared by a sequence involving 1) ozonation of pyrene at −78 degrees Celsius 2) careful reduction of the resulting ozonide by sodium iodide at −78 degrees Celsius 3) isolation and purification of the resulting 1,1'-biphenyl-2,2',6,6'-tetracarboxaldehyde 4) reduction of this by sodium borohydride to a tetra-alcohol derivative 5) conversion of the tetra-alcohol to a tetrabromide derivative with phosphorus tribromide 6) conversion of the tetrabromide to a tetrachloride using lithium chloride 7) reaction of the tetrachloride with lithium diphenylphosphide to prepare the final "tetraphosphine". The preparation to the tetrabromide was disclosed by Zhang in the reference of I. Agranet et. al. *J. Org. Chem.* 44, pp. 1936-1941 (1979)

Despite the improvements in the art, there remains a need to have an active hydroformylation catalyst that is stable for long periods of time that produces products with high N/Iso ratios and is economically accessible for commercial application.

SUMMARY OF INVENTION

According to an embodiment, the disclosure teaches a process for producing aldehydes, comprising contacting an olefin, with hydrogen and carbon monoxide in the presence of a catalyst composition to produce aldehydes, wherein the catalyst composition comprises a rhodium source and a tetradentate ligand, said tetradentate ligand comprising the following structure:

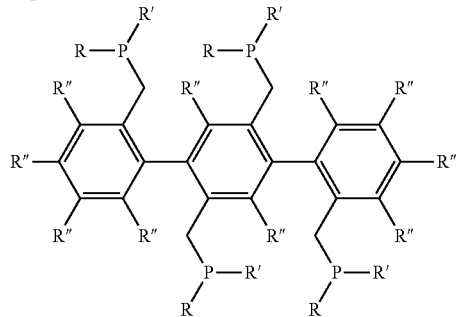

wherein,
R=aryl, arylalkyl, alkyl-substituted-aryl, hydrocarbyl alkyl, R optionally being substituted with heteroatom and other functional groups.
R'=aryl, arylalkyl, alkyl-substituted-aryl, hydrocarbyl alkyl, R' optionally being substituted with heteroatom and other functional groups.
R"=H, aryl, tertiary-butyl and heteroatom and other functional groups.
Heteroatom and other functional groups=F, thioethers, aryl or alkyl ethers, esters bound through the single oxygen bond, CF3, carboxylic acid esters, carboxylic amides and alkali metal salts of sulfonic acid.
P=Phosphorus Atom.
The process produces aldehydes in a Normal:Iso ratio of from about 15:1 up to about 100:1 or alternatively from about 15:1 up to about 50:1.

According to an alternative embodiment, the disclosure teaches a catalyst composition comprising a rhodium source and a tetradentate ligand comprising the following structure:

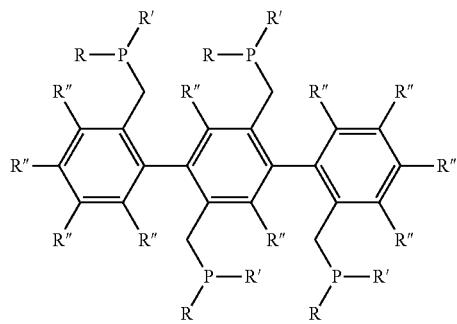

wherein,
R=aryl, arylalkyl, alkyl-substituted-aryl, hydrocarbyl alkyl, R optionally being substituted with heteroatom and other functional groups.
R'=aryl, arylalkyl, alkyl-substituted-aryl, hydrocarbyl alkyl, R' optionally being substituted with heteroatom and other functional groups.
R"=H, aryl, tertiary-butyl and heteroatom and other functional groups.
Heteroatom and other functional groups=F, thioethers, aryl or alkyl ethers, esters bound through the single oxygen bond, CF3, carboxylic acid esters, carboxylic amides and alkali metal salts of sulfonic acid.
P=Phosphorus Atom.

According to another alternative embodiment, the disclosure teaches a tetradentate ligand adapted for use with a catalyst composition, the tetradentate ligand comprising the following structure:

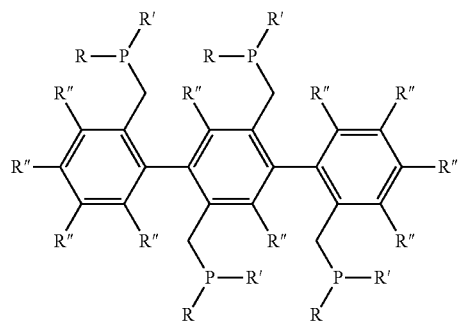

wherein
R=Phenyl.
R'=Phenyl
R"=H
P=Phosphorus Atom

DETAILED DESCRIPTION OF INVENTION

This disclosure teaches a low-pressure rhodium-based hydroformylation catalyst that is used in combination with a tetradentate triorganophosphine ligand that is capable of producing hydroformylation products with high linear/branched product ratios and is stable to long-term operation at relatively high reaction temperatures. The tetradentate ligand of this invention represents a new composition of matter and is specific in its ability to modify the rhodium hydroformylation catalyst to produce aldehyde products with high linear/branched ratios. Likewise, the precursor to this composition of matter, namely 2,2',2",5'-tetramethyl-1,1':4'-1"-terphenyl, is available by the aryl coupling reaction of 2-chloromagnesium- or 2-bromomagnesiumtoluene with either 2,5-dibromo- or 2,5-dichloro-1,4-dimethylbenzene, derivatives of para-xylene.

The tetradentate ligand of the invention has one hydrogen atom of each of the four benzylic methyl groups of the terphenyl rings substituted with an R, R' di-organophosphine moiety. The R,R' groups may be the same or different and may be aryl, arylalkyl, alkyl-substituted-aryl or hydrocarbyl alkyl. Likewise, the R,R' groups may have substitution present with heteroatom groups such as ethers, fluoro, carboxylate esters, carboxylic acid amides and the like, as long as the substituents do not act as poisons to the hydroformylation reaction. Likewise, the terphenyl rings may also have substitution R" for the available positions not occupied by the 2,2',2"',5'-tetrakis(R,R'-phosphinomethyl) groups. These could include in addition to H, such groups as aryl, t-butyl and heteroatom groups enumerated above, provided these groups do not act as poisons to the hydroformylation reaction.

It is very important for the success of the catalyst, that the purity of the tetradentate ligand be free of certain isomer impurities that act as poisons. Thus, it is desirable that no impurities are present, for example, having two (R,R'-phosphinomethyl) moieties located in a meta position to each other on the outside phenyl rings of the 1,1':4',1"-terphenyl backbone. This configuration results in a totally inactive hydroformylation catalyst. Examples of such poisons would include 2,2',2",4-tetrakis(R,R'-phosphinomethyl)-1,1':4',1"-terphenyl and 2,2',3",5'-tetrakis(R,R'-phosphinomethyl)-1,1':4',1"-terphenyl among others.

Other impurities that may be either tridentate or pentadentate ligands would be considered poisons if they have any R,R'-phosphinomethyl moieties present on one of the aromatic rings in a meta configuration to each other. By way of non-limiting example, this would include 2,2',4-tris(R,R'-phosphinomethyl)-5'-methyl-1,1':4',1"-terphenyl and 2,2', 2",4,5'-pentakis(R,R'-phosphinomethyl)-1,1':4',1"-terphenyl and others fitting the meta criterion. It is desirable that the 2,2',2",5'-tetrakis(R,R'-phosphinomethyl) ligand of this disclosure be preponderant in the ligand mixture present in the catalyst solution by having four bonding sites available on the molecule with minimal oxo-active tridentate or pentadentate impurities present that may lessen the efficiency of the catalyst to produce aldehyde product with high linear/branched ratios. The general description of the tetradentate ligand of this disclosure is shown below.

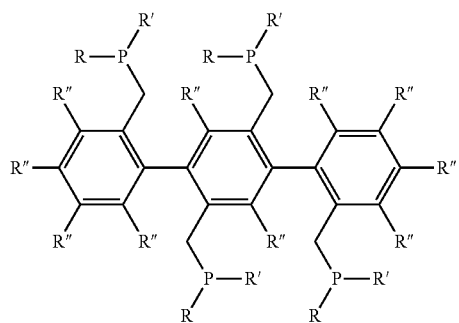

R, R' and R" are as described in the body of this application.

The mole ratio of the tetradentate ligand of this disclosure to rhodium present in the reactor should be at least 0.5/1 to form an active catalyst capable of hydroformylating linear olefins to aldehyde products having high linear/branched ratios. Normally, an excess of ligand is used as a buffer against losses of ligand due to traces of oxygen present in reactor feeds. Thus the mole ratios can be as high as 50/1 or greater down to 1.5/1, with desirable ranges from 2/1 to 15/1 or 3/1 to 12/1. The concentration of rhodium present in the reactor may vary from about 1 mg rhodium/liter up to about 500 mg rhodium or more/liter. The catalyst activity and the high cost of rhodium makes the desirable concentrations typically in the 50 mg rhodium/liter to 300 mg rhodium/liter range.

Just about any source of rhodium may be used, provided it can dissolve and form an active complex with the ligand of this invention, and that associated anions with the rhodium do not act as poisons to the hydroformylation reaction. Thus salts of rhodium such as rhodium trichloride, sulfate, acetate, 2-ethylhexanoate and the like may be used. Other sources may include complexes such as $Rh_2(I)(CO)_4(Cl)_2$, tris(triphenylphosphine)Rh(CO)H, $Rh_6(CO)_{16}$, $Rh_4(CO)_{12}$ and Rh(I)acetylacetonato$(CO)_2$. The desirable sources of rhodium are those which do not introduce anions that can lead to the formation of strong mineral acids. Thus, desirable sources of rhodium would include rhodium salts of carboxylic acids such as the acetate and 2-ethylhexanoate, and rhodium carbonyl complex species free of chloride such as the Rh(I)acetylacetonato$(CO)_2$ and the zero-valent rhodium carbonyl complexes. Tris(triphenylphosphine)Rh(CO)H could also be used.

The reactor design can be of any typical of use in the art of hydroformylation. Thus, the reactor can be a batch autoclave; a bubble column reactor with liquid overflow and liquid catalyst recycle; a stirred tank reactor with gas stripping to take volatile aldehyde product overhead from a standing high boiling liquid phase containing the catalyst; a bubble column gas stripped reactor and the like.

The mole ratio of olefin to rhodium present in the reactor in the case of a batch autoclave may be typically 10,000/1 or more down to as little as 100/1. Due to economic reasons of the cost of rhodium, the olefin/Rh mole ratio is desired to be as high as possible in the 2000/1 to 10,000/1 range. In the case of continuous feed and product removal reactors where the ratio of olefin/rhodium present in the reactor is not as easily determined, the mole ratio of olefin fed/hour to the moles of rhodium present in the reactor may range from 1,000,000/1 or more down to 1,000/1 with typical ranges of 300,000/1 to 50,000/1, especially when propylene is used as the linear olefin.

The reactor vapor is composed of hydrogen, carbon monoxide, any inert gases present in addition to volatile olefin to form the total reactor pressure. In practice, the low pressure hydroformylation catalyst of this invention can operate at gage pressures of 500 psig (3446 kPa) or more down to 14.7 psig (101.3 kPa). The preferred pressure ranges are from 100 psig (689 kPa) up to 300 psig (2068 kPa).

The amount of reactant present in the reactor vapor space is important for the catalyst of this disclosure. This is normally measured as the absolute partial pressures of the individual reactants present in the reactor exit gas on an aldehyde-free basis. Using standard engineering calculations, the partial pressures can be determined by standard analytical procedures such as gas chromatographic analysis in combination with a measure of the reactor pressure. The pressures are expressed in absolute partial pressure, which includes the additional 1 atmosphere pressure over and above gage pressure. The partial pressures of each component are calculated by determining the mole fraction ($X_a$) for a reactant "a" present in the exit gas and multiplying this by the absolute pressure in the reactor. Thus, for carbon monoxide representing 25 mole percent ($X_{co}$=0.25) of the exit gas composition, and a reactor pressure of 260 psi gage (1792 kPa), the absolute partial pressure would be:

CO partial pressure=0.25×(260+14.7 psi gage)=68.7 psi absolute (473 kPa absolute)

Other reactants such as hydrogen and propylene in the case of butyraldehyde production would be calculated in a similar manner.

The reactor exit partial pressure ranges of carbon monoxide and hydrogen when measured in the reactor gage pressure range of 100 psig to 300 psig (689-2068 kPa), which may range from 10 to 150 psi absolute (69-1034 kPa) for carbon monoxide and 30-150 psi absolute (207-1034 kPa) for hydrogen. The more desirable ranges are 20 to 40 psi absolute (138-276 kPa) for carbon monoxide and 40-130 psi absolute (276-896 kPa) for hydrogen. Ranges of absolute partial pressure of 25-35 psi absolute (172-241 kPa) for carbon monoxide and 50-100 psi absolute (345-689 kPa) for hydrogen are also desirable.

In the special case of propylene hydroformylation, where the olefin exists as a vapor, the partial pressures of propylene in the reactor exit gas are 30 to 160 psi absolute (207-1143 kPa) and in an alternative embodiment 50-100 psi absolute (345-848 kPa). The partial pressures of carbon monoxide and hydrogen when hydroformylating propylene are the same as listed previously for all linear olefin hydroformylation.

The partial pressures of inert materials in the reactor exit gas do not influence the performance of the catalyst to any significant degree provided the partial pressure ranges of carbon monoxide, hydrogen, and in the case of butyraldehyde production, propylene are used.

The reactor temperature influences both the catalyst activity, usually measured by the amount of aldehyde product produced per hour per gram of rhodium catalyst present in the reactor, and rate of loss of catalyst activity by intrinsic catalyst deactivation. Both catalyst activity and rate of catalyst deactivation increase with increasing reactor temperature. Thus, the reactor temperature may range from 25 degrees Celsius up to 140 degrees Celsius to perform the hydroformylation reaction. In alternative embodiments, the temperature range is 80 to 125 degrees Celsius or from 90 to 110 degrees Celsius.

The olefin feed can be any alpha-olefin, including propylene, 1-butene, 1-pentene, 1-hexene, 1-octene, 1-nonene, 1-decene and the like where the desirability of having linear aldehyde products is of most value. Likewise, di-olefins such as 1,8-octadiene and other similar alpha-omega linear unconjugated dienes may be used to prepare linear dialdehyde derivatives.

Internal olefins such as cis and trans-butene-2 and cis and trans-octene-2, and similar internal olefins, may be considered as feeds with the catalyst of this invention. Conditions have been explored in the literature that indicate that under certain hydroformylation conditions, internal olefin isomerization can lead to the preparation of linear aldehyde product from these types of materials as mentioned by X. Zhang et. al. "*J. Amer. Chem. Soc.*" 2006, 128, 16058-16061.

Substitution by heteroatom-containing groups such as ethers, alcohols, esters with a single bond oxygen linkage to the hydrocarbon from the ester, fluoro, aromatic rings, alkyl groups, and other groups as defined above in R, R', R" may also be present on the olefin provided these groups do not act as poisons to the hydroformylation reaction. Ideally, to obtain the maximum benefit of having a highly selective catalyst for the preparation of linear aldehyde product, the positioning of substituents on the alpha olefin should be at least on the 3-carbon of the alpha olefin or further removed if the olefin is longer than three carbons. This could also include the bicyclic olefin 2-vinyl-bicyclo[2.2.1]-heptane, and other olefins like vinylcyclohexane, vinylcyclopentane, allyl alcohol, and the like.

Any liquid medium may be used as a solvent for use with a hydroformylation catalyst provided it is not a poison to the hydroformylation reaction. Thus, the solvent may include, aldehyde product, olefin feed, hydrocarbons, aromatic hydrocarbons, alcohols, esters, ethers, aldol condensation products of the aldehyde product produced, substituted carboxylic amides and mixtures of each. The choice of solvent may be dependent on the specific feed being hydroformylated and the design of the reactor involved. Higher boiling solvents would be preferred, for example, in a reactor using gas stripping vapor take-off for removal of lower boiling aldehyde product. The catalyst of this invention is advantaged as it is not decomposed by the action of aldehyde or hydroxyl-containing co-products present in the reactor.

EXAMPLES

General Analytical Methods:

A Hewlett-Packard 5890 auto injector FID gas chromatograph equipped with a 30 m×0.32 mm ID DB-5 medium film capillary column was used for laboratory and product sample analyses. $^1$H Proton NMR and $^{31}$P NMR spectra were carried out using an Oxford 400 NMR Spectrometer. Gas chromatographic-mass spectroscopic analyses were carried out using a 5975 XL B/CI MS D instrument.

Example 1

Preparation of 2,2',2",5'-Tetramethyl-1,1':4',1"-terphenyl Precursor by Reaction of 2-Chloromagnesiumtoluene with 2,5-Dibromo-p-xylene in the Presence of 10/1 TPP/NiBr2

This example represents a diarylation reaction that prepares a hydrocarbon precursor having four methyl groups in accordance with the composition of this invention.

A 1 liter three-necked flask was equipped with a Teflon coated magnetic stirrer, a glycol chilled reflux condenser with nitrogen atmosphere, a 500 milliliter pressure equalizing addition funnel, a thermocouple with readout, an optional heating mantle/hot water bath and a magnetic stirrer. The flask was charged with anhydrous NiBr2 0.55 grams/2.5 mmole, TPP (triphenylphosphine) 6.55 grams/25 mmole, 2,5-dibromo-p-xylene 52.8 grams/0.20 mole and 50 ml/44.3 grams of reagent grade o-xylene. The green solution of the NiBr2/TPP complex was formed by heating the mixture to reflux for thirty minutes. After cooling to 50 degrees Celsius, 150 ml of dry THF solvent was added. The 500 ml pressure equalizing addition funnel was charged with 400 ml of 1.0 molar 2-chloromagnesiumtoluene solution in THF/0.40 mole and placed on the center neck of the flask.

The coupling reaction was carried out at 50 degrees Celsius by the dropwise addition of the Grignard reactant to the flask over 2 hours and 45 minutes. The reaction mixture turned to red-orange and then brown during the course of the addition. Following the complete addition, the flask was stirred at 50 degrees Celsius for an extra hour and then cooled to ambient temperature.

The crude reaction product was treated with 35 ml of concentrated hydrochloric acid and 115 ml of deionized water followed by the addition of 3 ml of 50% aqueous hydrogen peroxide. After separation in a funnel, the organic layer was washed with two 100 ml portions of 1% aqueous NaCl solution. Toluene, 100 ml, had to be added during the washing step to prevent product crystallization from the solvent mixture.

The crude organic material was then stripped with nitrogen and then subjected to 0.5 kPa vacuum at 60 degrees C. to remove the bulk of the lower boiling impurities. The net weight of sticky pale yellow crystals was 73 grams. This material was dissolved in 200 ml of isomeric hexane at reflux and cooled with stirring to ambient temperature. The desired product crystallized. This was then filtered on a coarse glass frit and the crystals were washed with four 50 ml portions of isomeric hexane. After drying in vacuum, a net weight of 18.11 grams of desired white crystalline product, representing 31% of theoretical yield, was obtained. The material was 97% pure by gas chromatographic analysis.

The proton NMR spectrum in ppm relative to TMS: 2H (S) 6.98 ppm 2',5' aromatic C—H; 8H (overlapping doublets) 7.15-7.30 ppm aromatic C—H of outer rings; 6H (S) 2.12 ppm 2,2" benzylic CH3; 6H (S) 2.02 2',5' benzylic CH3.

Example 2

Tetra-bromination of 2,2',2",5'-Tetramethyl-1,1':4', 1"-terphenyl—Precursor to Ligand of this Invention The apparatus was a 1 liter flask was connected with a glycol chilled reflux condenser by way of "S" and straight "Y" adapters. The top of the reflux condenser had a "T" for nitrogen atmosphere and sweep across the top of the condenser. A 125 milliliter pressure equalizing addition funnel was placed on the other leg of the "Y" adapter. The flask had a Teflon coated magnetic stir bar, a heating mantle and a 250 watt "sun lamp" for irradiation of the contents of the flask.

The flask was charged with 2,2',2",5'-tetramethyl-1,1':4', 1"-terphenyl X-002250-090 14.32 grams/50 mmole and 250 ml of CH2Cl2. The 125 addition funnel was charged with molecular bromine 32.0 grams/10.26 ml/200 mmole and 40 ml of CH2Cl2 and mixed in place.

The reaction was carried out by heating the mixture with stirring to gentle reflux, turning on the sun lamp and then adding the bromine solution dropwise. The total addition time was 5 hours 5 minutes. The solution was irradiated an extra 3 minutes that removed all orange color from the CH2Cl2 down-comer. The reaction solution however remained a red color. The reflux was continued for an extra 20 minutes to drive out the dissolved HBr.

The crude solution was stripped with nitrogen at ambient temperature and then subjected to 4.7 mm Hg (0.62 kPa) pressure to remove all solvent. The net weight of the resulting yellow-orange "taffy" was 29.06 grams (theoretical weight 30.1 grams). The crude product was recrystallized from 60 ml of toluene heated to 80 deg C. and then cooling slowly while being stirred. A small amount of the retained "taffy" was used to seed the mixture at about 60 deg C. to induce crystallization. The slurry resulting was stirred at ambient temperature over the weekend before filtering on a coarse glass frit. The filter cake was washed with 2×10 ml of ambient temperature toluene, sucked dry and then subjected to 4.8 mm Hg (0.63 kPa) pressure to remove adhering solvent. The net weight of white powder was 11.75 grams (39% of theoretical weight). This material has ~5% solubility in CDCl3.

The 1H NMR spectrum is: 2H (S) 7.55 ppm 3',6'-aromatic C—H; 8H overlapping (DD) 7.35-7.50 ppm aromatic C—H; 4H (DD) 4.4 ppm J=0.15 ppm CH2-Br; 4H (DD) 4.2 ppm J=0.15 ppm CH2-Br. Trace impurities, CHBr2 benzal at 6.31 and 6.38 ppm, benzylic CH3 at 2.35, 2.16 and 2.12 ppm.

Example 3

Conversion of 2,2',2",5'-Tetra(bromomethyl)-1,1':4', 1"-terphenyl into 2,2',2",5'-Tetra(chloromethyl)-1,1': 4',1"-terphenyl by LiCl Exchange This is the direct precursor to a ligand of this invention. This is using recrystallized tetrabromo compound in a LiCl exchange reaction.

A 500 milliliter Ehrlenmeyer flask was used. The flask had a standard taper joint with stopper and a Teflon coated magnetic stir bar. The flask was purged with nitrogen prior to use. The flask was charged with recrystallized 2,2',2",5'-tetra(bromomethyl)-1,1':4',1"-terphenyl X-002250-095 9.03 grams/15 mmole and 200 ml of dry DMF (dimethylformamide). The material was stirred at ambient temperature forming a homogeneous solution. Powdered anhydrous LiCl 12.70 grams/300 mmole was added to the stirred mixture in portions at ambient temperature. This was stirred 40 hours at ambient temperature. The mixture was homogeneous at the end of this period.

The mixture was chilled externally with a water-ice bath and treated with 75 ml of cold 5% aqueous HCl that formed two layers. Diethyl ether (150 ml) was added that also formed a two layer mixture but contained a crystalline suspension of product. The layers were separated with the suspension remaining with the ether extract. The aqueous layer was re-extracted with 2×100 ml of diethyl ether. The combined ether extracts were now homogeneous. This was washed with 2×50 ml of 80/20 v/v saturated NaCl/DI water solution.

The extract was dried with 100 grams of anhydrous Na2SO4 whereupon product began to precipitate. This was resolved by the addition of 100 ml of CH2Cl2. This was then filtered and the Na2SO4 cake was washed with 2×50 ml of CH2Cl2 to get a full account of the product formed.

After nitrogen stripping and subjecting the filtrate residue to 4.8 mm Hg (0.63 kPa) pressure, a net weight of 6.09 grams of white crystalline solid was obtained or 95.7% of the theoretical weight of tetra-chloro compound. A sample was dissolved in THF and analyzed by gas chromatography using the method disclosed in this report. The product had a retention time of 34.2 minutes and represented 80% of the high-boiling product peak area. Two smaller peaks representing 10% each of the area were observed at 31.25 and 32.0 minutes elution time and are suspected to be the two isomers of mono-methyl, trichloro-co-product.

The 1H NMR of the material is: 2H (DD) 7.60 ppm aromatic C—H; 2H (DD) 7.35 ppm 2',5' aromatic C—H(?); 6H overlapping (DD) 7.40-7.50 ppm aromatic C—H; 8H overlapping (DD) 4.25-4.50 ppm CH2-Cl; Impurities observed tr. CH2Cl2 5.28 ppm; tr. 2.12 and 2.15 ppm benzylic CH3.

Example 4

Preparation of 2,2',2",5'-Tetrakis(diphenylphosphinomethyl)-1,1':4',1"-terphenyl—Ligand of this Invention's Composition—Using the Tetra-Chloro Precursor The apparatus was a 250 milliliter three-necked flask equipped with a Teflon coated magnetic stir bar, a nitrogen atmosphere, a 50 milliliter pressure equalizing addition funnel and an optional water ice bath. All handling for charging the flask and funnel were carried out in a nitrogen glove box. All solvents and reagents were purged with nitrogen prior to use.

The 250 ml flask was charged with 7.44 grams/6.95 ml/40 mmole of diphenylphosphine, 80 ml of dry THF solvent and then charged with 2.0 M n-butyllithium in cyclohexane 20 ml/40 mmole over ten minutes at ambient temperature to form the red-orange solution of lithium diphenylphosphide anion. The 50 ml addition funnel was charged with 2,2',2", 5'-tetra(chloromethyl)-1,1':4',1"-terphenyl 4.24 grams/10 mmole and 40 ml of dry THF solvent. This amount of solvent was very close to the solubility limit, but all did eventually dissolve with gentle shaking. After this, the addition funnel was placed on the center neck of the flask.

The flask containing the lithium diphenylphosphide anion was chilled externally with a water-ice bath to the reaction temperature of 0 degrees C. The tetra-chloro reactant was added dropwise over 1 hour and 45 minutes to the vigorously stirred anion solution. The pale yellow endpoint was reached at 97% of the total addition. No further tetra-chloro reactant was added after this point. The solution was kept at 0 degrees for an additional 30 minutes when product was observed to begin precipitating, forming a light yellow but stirrable slurry. This was allowed to warm to ambient temperature and then stir overnight. The appearance was unchanged in the morning.

Toluene, 20 ml was added. The slurry did not dissolve. Aqueous 2% HCl, 50 ml was added and the slurry became more dense. This was transferred under nitrogen into a 500 ml separatory funnel and the mixture was heated and shaken to break the emulsion. A clear colorless aqueous layer was then separated and discarded. The organic layer was washed with 2×50 ml of 2% aqueous NaCl and then 50 ml of 0.5% aqueous NaCl. The separatory funnel had to be heated to break the emulsion and separate layers. After the last wash, the organic layer was two-phase with the clear colorless organic layer having a layer of white microcrystalline product sitting at the bottom of the layer. A sample of this solution was analyzed on a gas chromatograph. The material contained about 200 mg of unreacted diphenylphosphine (about 2.5% of original charge).

This was then drained into a tared round bottomed flask. Some of the white solid residue of product stuck to the walls of the separatory funnel. This was dissolved and washed into the flask after the addition of 20 ml of more toluene.

The solvents were removed by stripping with nitrogen and then subjecting the residue to 5.4 mm Hg (0.72 kPa) pressure while being heated to 50 degrees C. A net weight of 10.71 grams of crude crystalline product remained. The theoretical weight is 10.23 grams. A sample of this was dissolved in DCCl3 for NMR analysis. All material dissolved indicating that all salts had been removed. The ratio of CH2-PPh2/CH3 protons in the crude material were 1.00/0.33 indicating that tridentate ligand material is present as an impurity.

The crude material was triturated with 60 ml of isopropanol/10 ml toluene at reflux and cooling with stirring. This crystalline material was filtered and washed with three 25 ml portions of isopropanol and dried at 60 degrees C. at 5.4 mm Hg (0.72 kPa) pressure. The net weight of free-flowing product was 9.22 grams. The ratio of CH2-PPh2/CH3 was now 1.00/0.19. This material was tested in the oxo bench unit and had a stable activity of 5.89 lbs (2.67 Kg) HBu/g-Rh-hr with an average N/Iso ratio of 39.1/1. The recovered catalyst was yellow in color with some of the ligand precipitating from the cold catalyst solution.

31P absorptions relative to 85% aqueous H3PO4=−8.36 ppm (25P); −9.27 ppm, −9.23 ppm, −9.44 ppm (sum)(54P) and −11.13 ppm (20P) mix of tetradentate and possibly two isomers of tridentate.

1H NMR spectrum integrated area ratios=94.5H 6.9-7.35 ppm overlapping multiplets aromatic C—H from phenyls on phosphorus and some of the 1 and 1″ aromatic rings; 5.5H total 6.7 ppm (D) 6,6″, 6.5 ppm (D) 3,3″, 6.26 ppm (S) 3′,6′ aromatic C—H; 14.67H overlapping (DD) benzylic CH2-PPh2; 2.82H 2.35 ppm (S) —CH3.

Example 5

(*Comparative)—Preparation of 3,3′,5,5′-Tetrakis (diphenylphosphinomethyl)-1,1′-biphenyl—A Tetradentate Ligand not of this Invention's Composition This tetradentate ligand has two separate sites present that represent a meta configuration of two diphenylphosphinomethyl substituents to each other on the biphenyl rings that results in an inactive hydroformylation catalyst.

The apparatus and general procedure are that of Example 4. A 500 ml flask was charged with diphenylphosphine 7.44 grams/6.95 ml/40 mmole and THF solvent 100 ml. 2.0 Molar n-butyllithium in cyclohexane 20 ml/40 mmole was added to form a red-orange solution.

The precursor compounds 3,3′,5,5′-tetramethyl-1,1′-biphenyl, 3,3′,5,5′-tetrakis(bromomethyl)-1,1′-biphenyl and 3,3′,5,5′-tetrakis(chloromethyl)-1,1′-biphenyl were prepared from 3,5-dimethyl-1-bromobenzene using procedures similar to those of examples 1, 2 and 3.

A 50 ml addition funnel was charged with 3,3′,5,5′-tetrakis(chloromethyl)-1,1′-biphenyl and 30 ml of THF solvent forming a clear colorless solution. The funnel was placed in the center neck, directly over the vortex of the stirred anion solution. The flask was chilled with an external dry ice/isopropanol bath to −20 to −25 degrees C. The tetra-chloro solution was added dropwise at a rate that would complete addition in forty minutes. The yellow endpoint was reached at 72% of the total addition. No further addition of tetra-chloro solution was done following this.

The solution was allowed to warm to ambient temperature and then stood an extra ten days at ambient temperature under a nitrogen atmosphere. The color was unchanged after ten days.

The crude material was treated with 0.81 ml of absolute methanol followed by 20 ml of toluene and 50 ml of 8% aqueous HCl. Two clear colorless layers resulted. The acid was separated and disposed of. The organic layer was washed with two 50 ml portions of 2% aqueous NaCl.

The organic layer was stripped with nitrogen and then subjected to 5.4 mm Hg (0.72 kPa) pressure while being heated to 50 degree C. The resulting colorless turbid oil was 9.47 grams.

Several attempts were made to crystallize the symmetrical molecule from the crude mixture without success. The oil was triturated by heating to reflux and cooling to ambient temperature with the following mixtures of solvents. This was carried out under the strict exclusion of air. 60 ml isopropanol/20 ml toluene; 60 ml isomeric hexane/14 ml toluene; 30 ml isomeric hexane/7 ml toluene; 30 ml isomeric hexane. In each case, except the last, the oil dissolved completely at reflux and separated into a heavy oil phase and solvent phase when cooled. The solvent phase was removed and discarded. In this way about 2 grams of diphenylphosphine and most of the undesired tridentate ligand impurities were removed from the heavy oil.

The residual white residue set up into a hard white plastic appearing material. After subjecting the residue to vacuum, a net weight of 2.00 grams of essentially pure product was obtained. This is 21% of expected yield.

No hydroformylation catalytic activity was observed using the ligand of this Example.

31P absorptions relative to 85% aqueous H3PO4 (P integration relative ratios)=−9.15 ppm (100P) product; +30 ppm (4.7P) —CH2-P=O-Ph2; +22 ppm diphenylphosphine oxide (0.9P); +14.3 ppm tetraphenyldiphosphine (0.7P); +39.7 ppm (0.1P) diphenylphosphine.

1H NMR spectrum integration expressed as protons in the molecule=40H 7.5 ppm broad (S) phenyl C—H attached to phosphorus; 2H 6.8 ppm (S) 4,4' aromatic C—H; 4H 6.5 ppm (S) 2,2',6,6' aromatic C—H; 7.5H 3.35 ppm (S) benzylic CH2-PPh2; 0.5H total 2.35 and 2.2 ppm (S) CH3.

Example 6

(Comparative)—Preparation of 2,2',5-Tris(diphenylphosphinomethyl)-1,1-biphenyl—A Tridentate Ligand not of this Invention's Composition This is an example of a tridentate ligand that is catalytically active and not consistent with the composition of this invention. The N/Iso ratio of product is lower than the example of this invention.

The chemical precursors for this comparative example were prepared in a similar manner to those described in Examples 1, 2 and 3. Thus, 2,2',5-trimethyl-1,1'biphenyl was prepared by the NiBr2/TPP catalyzed coupling reaction of 2-chloromagnesium toluene with 2-bromo-1,4-dimethylbenzene, the 2,2',5-tris(chloromethyl)-1,1'-biphenyl was made by a combination of bromination followed by chloride exchange of the crude bromo-intermediate with lithium chloride.

The apparatus and the general procedure were the same as described in example 4. The 250 ml flask was charged with diphenylphosphine 8.37 grams/7.62 ml/45 mmole, dry THF solvent 80 ml. 2.0 Molar n-butyllithium in cyclohexane 23.5 ml/45 mmole was added by syringe. This addition had an extra 1.0 ml added to scavenge traces of moisture in the solvent to just form a yellow color. The end solution was the normal red-orange color.

The 50 ml addition funnel was charged with 2,2',5-tri (chloromethyl)-1,1'-biphenyl 4.49 grams/15 mmole and 40 ml of dry THF solvent to form a clear colorless solution. The addition funnel was placed in the center neck of the flask above the vortex.

The flask was chilled with an external water ice bath to 0 degrees C. The tri-chloro solution was added dropwise over one hour. All tri-chloro solution was added. The color changes went from red-orange through red-brown and then lightening to brownish yellow at the end. The mixture was allowed to warm to ambient temperature with stirring and remain at that temperature overnight. The color in the morning was now a brown-shade orange.

The reaction was quenched with 1.82 ml (45 mmole) of absolute methanol in small increments from a syringe. The color turned to a light yellow after the addition of 0.10 ml (2.5 mmole of CH3OH) and remained the same color throughout the rest of the methanol addition. The mixture was then treated with 20 ml of toluene and 50 ml of 2% aqueous HCl. Two colorless and clear layers resulted. A sample of the organic phase was analyzed on the gas chromatograph. The organic layer contains 0.80 gram of unreacted diphenylphosphine (about 10% of the original charge) and 0.26 grams of diphenylphosphine oxide. The aqueous layer was disposed of and the organic phase was washed with 2×50 ml of 2% aqueous NaCl.

The organic layer was dried with 10 grams of anhydrous Na2SO4, filtered and the cake washed with 20 ml of THF into a tared round bottomed flask. The solvent was removed by nitrogen stripping and subjecting the residue to "full" vacuum with heating to 50 degrees C. The net weight of crude pale yellow heavy oil was 10.09 grams.

The oil was triturated with 20 and then 40 ml of isomeric hexane heated to reflux and cooling to ambient temperature. The separate hexane phase was decanted from the heavy oil product in each case. The oil solidified to a sticky white solid. The combined hexane extracts were analyzed on the gas chromatograph. A total of 0.42 grams of diphenylphosphine had been removed.

The white solid was broken up and washed with 2×10 ml of isomeric hexane and then subjected to "full" vacuum. The solid puffed out to a "cotton candy" material that was subjected to vacuum for about 30 minutes to remove volatiles. Upon removing the vacuum, a brittle mass resulted that was easily pulverized to free-flowing powder. The net weight of this material was 6.63 grams vs a theoretical weight of 11.22 grams, or 59% of theory if pure.

This catalyst ligand was tested in the oxo bench unit and had an activity of 1.25 lbHBu/g-Rh-hr with a N/Iso ratio of 13.7/1. The catalyst returned a "medium orange" color.

31P absorptions relative to 85% aqueous H3PO4 (P relative integrated areas)=−9.04 ppm (50P), −9.49 ppm (100P) desired product. Impurities: +22 ppm diphenylphosphine oxide (7.5P); −14.3 ppm tetraphenyldiphosphine (2P); −39.7 ppm diphenylphosphine (0.7P)

1H NMR spectrum (H integrated area ratios)=100H 6.75-8.0 ppm overlapping multiplets aromatic C—H; 13.1H 3.2-3.6 ppm overlapping (DD) benzylic CH2-PPh2; 1.1H 2.35 ppm (S) CH3. The integrated ratio of CH2-PPh2 to CH3 protons was 1.00/0.09 indicating little bidentate ligand impurity is present.

Example 7

(Comparative)—Other Catalyst Ligands

Other organophosphorus ligands used in comparative examples in this application were either purchased from laboratory reagent supply houses or were prepared by methods available from the open literature or patents.

Example 8

Description of the Oxo Bench Test Unit and General Operation:

The reactor is a 4 foot×1" diameter (122 cm×2.54 cm diameter) stainless steel bubble column. The bottom of the reactor has a stainless steel frit in the bottom for the introduction of reactant gases. The reactor has a differential pressure cell for the rough measurement of liquid level inside the reactor and a manifold at the bottom of the reactor for the charging of the catalyst solution. The reactor also has a plug at the top of the reactor for solvent clean out and an internal thermocouple for the measure of the reaction catalyst solution. The reactor has a jacket containing heating fluid to control reactor temperature. The heating fluid is controlled by an electric circulating hot oil heater. The temperature of the heating solution is also recorded by thermocouple.

The catalyst is charged to the reactor from 1 liter stainless steel "bomb" type cylinders. The preparation of catalyst solution and handling of the cylinders for charging is normally carried out in nitrogen glove boxes to exclude air contamination. The bombs are thoroughly cleaned with acetone and/or other solvents and dried with nitrogen prior to charging catalyst. The catalyst is charged using nitrogen pressure from the bomb to the reactor via the manifold at the bottom of the reactor. All connecting lines are cleaned with solvent and dried with nitrogen before this is done. At the completion of the run, catalyst is allowed to be pressured back through the manifold from the reactor into the "bomb".

The feeds to the unit include aluminum cylinders of 1/1 vol/vol H2/CO purchased from vendors and of certified composition; zero grade hydrogen and nitrogen cylinders. The nitrogen and hydrogen are normally run together through a Pd/Al2O3 "Deoxo" bed to remove traces of oxygen in the nitrogen after leaving the controllers. Brooks Mass Flow controllers are used to feed these gases. Flows are typically recalibrated if the unit has not been operated over several months. Propylene is fed by a liquid feed system. The propylene is then heated down-stream to vaporize it at pressure prior to contacting the other gases and entering the reactor via the frit.

The reactor effluent gases are passed overhead through a glycol-chilled hairpin type condenser and drained into a vapor liquid separator (V/L) that is also glycol-chilled. Liquid product accumulates in this vessel and is drained hourly when under operation. Uncondensed gases pass out the top of the V/L through a pressure control valve that controls reactor pressure and let down to atmospheric pressure where the gas passes through a series of three dry ice traps. Condensate from these three traps is also collected hourly and combined with the material from the V/L. The hourly samples are allowed to degas at ambient temperature for several hours to allow the large majority of dissolved propylene to evaporate. After this, the net weight of product produced in the hour is determined and then analyzed by gas chromatography to determine the weight of aldehyde present and the N/Iso ratio of the resulting product. In practice, five hour runs are used for testing a given catalyst with the last three hours of product and data used for determining catalyst activity and N/Iso ratio.

Example 9

Standard BISBI/Rh Day-Long Run (2,2'-Bis(diphenylphosphinomethyl)-1,1-biphenyl) A Ligand not of this Invention This is an example of standard oxo bench unit conditions used. The flows, reactor temperature, reactor pressure of this example will be used for all comparative examples and example of the invention.

The catalyst solution was prepared in the nitrogen glove box. Rh(I)AcAc(CO)2, (rhodium(I)acetylacetonate dicarbonyl) 37.5 mg/0.1455 mmole containing 0.0150 grams of Rh, purified BISBI 0.96 grams/1.75 mmole and 190 ml of Texanol (2,2,4-trimethylpentane-1,3-diol mono isobutyrate) were dissolved together at ambient temperature. The purple-green crystals of the rhodium compound dissolved when contacting the BISBI and formed an orange solution. This is charged into the clean 1 liter bomb and the bomb connected to the bench unit.

The contents of the bomb was pressured into the reactor after connecting to the manifold with 100 psig (689 kPa) nitrogen and the process was repeated twice more to chase all liquid out of the bomb. The valves were opened slowly to keep from burping catalyst out the top of the reactor.

The reactor was then pressured to 260 psig (1792 kPa) with nitrogen and initiation of reactor catalyst solution heating was begun. After initiating heating, the gas flows were changed to the following:

H2=2.55 standard liters/min

1/1 v/v H2/CO=2.18 standard liters/min

N2=2.36 standard liters/min

When the reactor solution attained 105 degrees C., the heating was then stopped at 105 degrees and propylene feed was started at 356 grams propylene/hour.

The reactor was allowed to "walk" up to the target reaction temperature of 110 degree C. by allowing heat of reaction to bring it up. The hot oil bath temperature was adjusted to hold the reaction liquid temperature at 110 degrees C.

The run is officially started when the catalyst solution reaches the target reaction temperature of 110 degrees C. Data on operation is recorded hourly that includes flow settings, reaction temperature and pressure, bath temperature, reactor level and propylene tank level. Product samples are collected hourly as described in the general description of the unit. Normally, the reactor level is stable after the second hourly sample. The last three hours of samples are used to calculate the catalyst activity and N/Iso ratio. In this run, the average amount of butyraldehyde made per hour was 81.47 grams equivalent to 11.97 lb HBu/g-Rh-hr (5.43 kg Hbu/g-Rh-hr) with a N/Iso ratio of 57.9/1. The CO conversion per pass was 35.2% and the average partial pressures across the reactor were: 100.9 psia (695 kPa absolute) H2; 26.3 psia (181 kPa absolute) CO; 78.8 psia (543 kPa absolute) propylene and 69.1 psia (476 kPa absolute) nitrogen. The average reactor exit gas partial pressures were: H2=101.5 psia (670 kPa absolute); CO=22.0 psia (152 kPa absolute); propylene=77.7 psia (536 kPa absolute).

After the fifth sample is collected, the reactor was shut down. Propylene flow was shut off. The reactor was stripped for 15 minutes with the other flows being held constant to remove excess butyraldehyde from the catalyst solution. After the 15 minute period, the remaining flows were set to 1 liter/minute each and the reactor is cooled to 60 degree C. When reaching 60 degrees, the catalyst solution was allowed to pressure back into the bomb. The recovered catalyst is removed from the bomb in the nitrogen glove box, measured for retained weight and its color noted. The color was "medium Yellow color, clear".

The reactor and 1 liter bomb were cleaned and purged with nitrogen in preparation for the next run.

Example 10

Day-Long Run Using Catalyst of this Invention 2,2',2'',5'-Tetrakis(diphenylphosphinomethyl)-1,1':4', 1''terphenyl A catalyst mixture was prepared in the nitrogen glove box with 37.5 milligrams of Rh(I)AcAc(CO)2 containing 0.015 grams (0.1455 mmole) of rhodium, 1.79 grams (1.75 mmole) of 2,2',2'',5'-tetrakis(diphenylphosphinomethyl)-1, 1':4',1''-terphenyl from example 4 and 190 milliliters of Texanol solvent. Toluene 20 ml and THF 20 ml were added in an attempt to dissolve the ligand. The Rh(I)AcAc(CO)2 dissolved by reacting with the ligand forming a pastel yellow mixture with the undissolved ligand. This was stirred overnight in the nitrogen glove box in a stoppered Ehrlenmeyer flask. A thin stirrable suspension of ligand was present. This was added to the 1 liter sample bomb and charged to the bench unit reactor as previously described.

The reactor was operated at the conditions of example 9 for five hours. The average amount of butyraldehyde produced per hour in the last three hours was 40.04 grams with a N/Iso ratio of 39.1/1. This represents an activity of 5.89 lbs butyraldehyde/gram Rh-hour (2.67 kg HBu/g-Rh-hr). The CO conversion/pass was 17.3%. The average partial pressures across the reactor were: H2=100.7 psia (694 kPa absolute); CO=28.3 psia (195 kPa absolute); propylene=79.0 psia (545 kPa absolute). The reactor exit partial pressures were: H2=100.9 psia (695 kPa absolute); CO=26.4 psia (182 kPa absolute); propylene=78.6 psia (542 kPa absolute).

The color of the recovered catalyst was "pastel yellow, cloudy". The cloudiness was due to the precipitation of the ligand from catalyst solution upon cooling.

Example 11

(Comparative)—Day-Long Run Using a Tridentate Ligand not of this Invention 2,2',5-Tris(diphenylphosphinomethyl)-1,1'-biphenyl A catalyst solution was prepared in a nitrogen glove box from 37.5 milligrams of Rh(I)AcAc(CO)2 containing 15 mg of Rh (0.1455 mmole) and 1.31 grams 1.75 mmole of 2,2',5-tris(diphenylphosphinomethyl)-1,1'-biphenyl from example 6 and 190 milliliters of Texanol solvent. The feed catalyst solution was homogeneous yellow. The reactor was charged and operated under the conditions described in example 9. The run was carried out for five hours.

The reaction produced an average of 8.50 grams of butyraldehyde per hour or 1.25 lbs butyraldehyde/gram-Rh-hr (0.57 kg HBu/g-Rh-hr). The N/Iso ratio was 13.7/1. The color of the recovered catalyst was "medium orange, clear".

Example 12

(Comparative)—Day-Long Run Using a Tetradentate Ligand not of this Invention Having Two Diphenylphosphinomethyl Groups Meta to Each Other Resulting in an Inactive Catalyst A catalyst solution was prepared in a nitrogen glove box from 37.5 milligrams of Rh(I)AcAc(CO)2 containing 15 mg of Rh (0.1455 mmole) and 1.59 grams 1.68 mmole of 3,3',5,5'-tetrakis(diphenylphosphinomethyl)-1,1'-biphenyl from example 5 and 190 milliliters of Texanol solvent. The resulting feed solution was "medium amber color" and was homogeneous.

The catalyst solution was charged to the bench unit reactor and operated at the conditions used in example 9 for five hours. The only material taken overhead was Texanol solvent with dissolved propylene. There was no trace of any butyraldehyde product which means that the catalyst was poisoned to a stable catalytically inactive rhodium compound. It is believed that this poisoning is not dues to any intrinsic deactivation, but is instead a result of the two Diphenylphosphinomethyl Groups being in the meta position relative to each other. The recovered catalyst solution was "nice yellow clear".

Example 13

Day-Long Run Using 1,3-Bis(diphenylphosphinomethyl)benzene a Bidentate Ligand Having Two Diphenylphosphinomethyl Groups Meta to Each Other Resulting in an Inactive Catalyst This example shows the intrinsic poisonous nature of having two Diphenylphosphinomethyl groups present in a meta position to each other on the same aromatic ring when used as a ligand for rhodium catalyzed hydroformylation.

A catalyst solution was prepared in a nitrogen glove box using 37.5 milligrams of Rh(I)AcAc(CO)2 containing 15 milligrams (0.1455 mmole) of rhodium, 0.83 grams, 1.75 mmole of 1,3-Bis(diphenylphosphinomethyl)benzene X-002250-122 and 190 milliliters of Texanol. The resulting catalyst solution was red and clear.

The catalyst solution was charged to the bench unit reactor and operated at conditions used in example 9 for five hours. There was no trace of any butyraldehyde product in the overhead product in all samples which means that the catalyst was poisoned to a stable catalytically inactive rhodium compound. It is believed that this poisoning is not due to intrinsic deactivation, but is instead a result of the two Diphenylphosphinomethyl Groups being in the meta position relative to each other. The recovered catalyst was "bright yellow in color, clear".

Example 14

Table of Day-Long Runs Comparing Different Catalyst Ligands at the Conditions Used in Example 9

This table is a direct comparison of different catalyst ligands at the conditions used in example 9 to compare catalyst activities and N/Iso ratios produced. The amount of bidentate, tridentate and tetradentate ligand charged is 1.75 mmole unless noted otherwise. In runs using monodentate ligands, 3.50 mmole is used in an effort to maintain a constant amount of phosphorus available for bonding to rhodium. The amount of rhodium used was 37.5 milligrams of Rh(I)AcAc(CO)2, 15 milligrams of Rh, 0.1455 mmole. 190 milliliters of Texanol solvent was used to dissolve the mixture. The average absolute CO partial pressures across the reactor and the absolute CO partial pressures exiting the reactor are also included as CO partial pressure is known to influence N/Iso ratio.

Although not wished to be bound by any particular theory, with the exceptions of Example 12 and 13 above, it is believed that lighter colors in the below Table generally indicate higher catalyst stability and darker colors indicate less stability.

TABLE 1

Comparison of Different Ligands on Catalyst Activity and Butryaldehyde N/Iso Ratio at Reaction Conditions of Example 9

| Run | Ligand | L mmole | Activity KgHbu/ gRh-hr | N/Iso Ratio | Ave. CO PP kPa | Reactor exit CO PP kPa | Recov. Cat. color |
|---|---|---|---|---|---|---|---|
| Ex 9 | A | 1.75 | 5.43 | 57.9 | 181 | 152 | Med yellow |
| Ex 10 | B | 1.75 | 2.46 | 30.5 | 196 | 184 | Light yellow |
| Ex 11 | C | 1.75 | 0.57 | 13.7 | 205 | 202 | Med orange |
| Ex 12 | D | 1.68 | 0.00 | N/A | 207 | 207 | Nice yellow |
| Ex 13 | E | 1.75 | 0.00 | N/A | 207 | 207 | Bright yellow |
| 2236-014 | F | 1.75 | 0.32 | 43.3 | 205 | 204 | Med amber |
| 2236-008 | G | 1.75 | 2.70 | 2.28 | 194 | 181 | Light yellow |
| 2236-010 | H | 1.75 | 0.71 | 2.35 | 203 | 200 | N/R |

TABLE 1-continued

Comparison of Different Ligands on Catalyst Activity and
Butyraldehyde N/Iso Ratio at Reaction Conditions of Example 9

| Run | Ligand | L mmole | Activity KgHbu/ gRh-hr | N/Iso Ratio | Ave. CO PP kPa | Reactor exit CO PP kPa | Recov. Cat. color |
|---|---|---|---|---|---|---|---|
| 2236-011 | I | 1.75 | 1.13 | 4.24 | 201 | 196 | Norm dk orange |
| 2236-015 | J | 0.72 | 3.39 | 3.87 | 192 | 175 | Med yellow amber |
| 2265-110 | K | 1.75 | 1.30 | 16.3 | 201 | 188 | orange |
| 2265-106 | L | 1.75 | 0.27 | 4.03 | 206 | 205 | Light orange |
| 2236-009 | M | 3.50 | 4.84 | 2.06 | 183 | 158 | Med yellow |
| 2265-094 | N | 3.50 | 6.25 | 2.71 | 177 | 142 | Light amber gold |

Key to Ligands Used in Table:
A = 2,2'-bis(diphenylphosphinomethyl)-1,1'-biphenyl prepared by methods disclosed in U.S. Pat. No. 4,694,109
B = 2,2',2",5'-tetrakis(diphenylphosphinomethyl)-1,1':4',1"-terphenyl - Example 4
C = 2,2',5-tris(diphenylphosphinomethyl)-1,1'-biphenyl - Example 6
D = 3,3',5,5'-tetrakis(diphenylphosphinomethyl)-1,1'-biphenyl - Example 5
E = 1,3-bis(diphenylphosphinomethyl)benzene which was prepared by the reaction of lithium diphenylphosphide and alpha, alpha'-dichloro-metaxylene.
F = 2,2'-bis(dibenzophospholylmethyl)-5,5'-di-t-butyl-1,1'-biphenyl - prepared by methods disclosed in U.S. Pat. No. 5,332,846
G = 1,2-bis(diphenylphosphinomethyl)benzene - prepared by methods disclosed in U.S. Pat. No. 4,960,949
H = 1,4-bis(diphenylphosphino)butane which was purchased from Aldrich Chemical Co.
I = 1,1'-bis(diphenylphosphino)ferrocene - disclosed in U.S. Pat. No. 4,193,943 and purchased from Aldrich Chemical Co.
J = R,S-DIOP - U.S. 4,306,082 which was purchased from Aldrich Chemical Co.
K = XANTPHOS 4,5-bis(diphenylphosphino)-9,9-dimethylxanthene - P.W.N.M. Van Leeuwen et.al. *Organometallics* 14, pp. 3081-3089 (1995) Prepared in accordance with this journal article.
L = 2,2'-bis(diphenylphosphino)diphenyl available from Strem Chemical Co.
M - Benzyldiphenylphosphine available from Strem Chemical Co.
N - Triphenylphosphine which was purchased from Aldrich Chemical Co.

Example 15

Three-Day Run Demonstrating the Stability of the Catalyst of this Invention

This example uses the catalyst of this invention in a three-day run using conditions of Example 9. Between days, the unit is shut-down overnight and restarted in the morning, a procedure that also subjects low-pressure oxo catalysts to increased deactivation. The last three hours of each operating day are used to calculate the catalyst activity and N/Iso ratio for that day.

A catalyst mixture was prepared in the nitrogen glove box using 2,2',2",5'-tetrakis(diphenylphosphinomethyl)-1,1':4',1"-terphenyl, material from example 4, 1.79 grams, 1.75 mmole, Rh(I)acetylacetonate dicarbonyl 37.5 mg, 0.1455 mmole equivalent to 15 mg of rhodium, 190 milliliters of Texanol solvent and 20 ml of dry toluene as solvent. The mixture, contained in a 500 ml stoppered Erlenmeyer flask was stirred with a magnetic stirrer inside the nitrogen box overnight. The green-violet crystals of the rhodium compound dissolved quickly upon stirring forming a pale yellow suspension of catalyst and undissolved ligand. The mixture was allowed to stir overnight helping to pulverize the undissolved ligand into a thin pale yellow slurry.

The catalyst mixture was charged into the reactor described in Example 8 using the 1 liter stainless steel bomb. The reactor pressure control was set to 260 psig (1792 kPa) and the reactor was pressured by setting the flow controllers in the following sequence: N2=2.36 standard liters/minute (SLM); 1/1 v/v H2/CO (syngas)=2.18 SLM and H2=2.55 SLM. At the same time, the heating system was set to bring the temperature to 105 degrees Celsius in the reactor. Upon reaching 105 degrees Celsius, the propylene feed was started at 356 grams/hour and the temperature was "walked" up to 110 degrees Celsius. The run officially started when the temperature reached 110 degrees Celsius.

The run was carried out for a total of five hours at the conditions described above with data and butyraldehyde product taken each hour as described in examples 8 and 9.

After the last sample was collected for Day 1, the reactor was shut down in the following manner:
1. Propylene feed was stopped and the other feeds continued to operate at target gas flow rates for fifteen minutes.
2. The gas feeds were adjusted to: N2=0.0 SLM; H2=1.0 SLM and syngas=1.0 SLM
3. Cool to 60 degrees Celsius
4. Upon reaching 60 degrees the settings were changed to H2=0.0 SLM and syngas=0.0 SLM and block in valves feeding reactor and exiting reactor were closed to hold the pressure at 260 psig (1792 kPa)
5. Allow to cool to ambient temperature under pressure overnight.

The next morning, the reactor was started up in the following manner:
1. Open the block valves to and from the reactor. Reactor pressure is set to 260 psig (1792 kPa).
2. Start the gas feeds in the following order: N2=2.36 SLM; syngas=2.18 SLM and H2=2.55 SLM.
3. Start heating the reactor to 105 degrees Celsius.
4. Upon reaching 105, start propylene feed at 356 grams/hour and "walk" the reactor temperature up to 110 degrees Celsius.
5. The start to Day 2's run is when the reaction temperature reaches 110 degrees Celsius.

The Day 2 run is carried out as in Day 1 for five hours with data and butyraldehyde product being collected on an hourly basis.

At the finish of Day 2, the reactor is shut down as described above and in the morning is also restarted as described above.

The Day 3 run is carried out as described in Day's 2 and 1 for five hours.

The reactor is shut down as described above to reach 60 degrees Celsius. At that point, the 1 liter stainless steel bomb is connected to the bottom of the reactor and the contents of the reactor are allowed to be pressured into to it with pressure in the reactor.

After the bomb cools in the nitrogen glove box, it is de-pressured and the recovered catalyst is drained from it. The recovered catalyst was a pale greenish-yellow with a milky suspension of precipitating ligand. There was no evidence of catalyst decomposition to Rh cluster products by the light color. The table below lists the catalyst performance during the last three hours of each day's run.

| Day | Act. Kg HBu/gRh-hr | N/Iso Ratio | Exit CO P.P. |
|---|---|---|---|
| 1 | 1.94 | 41.0 | 27.2 psia/187.5 kPa |
| 2 | 1.98 | 43.5 | 27.4 psia/188.8 kPa |
| 3 | 1.80 | 43.5 | 27.6 psia/190.2 kPa |

I claim:
1. A process for producing aldehydes, comprising contacting an olefin, with hydrogen and carbon monoxide in the presence of a catalyst composition to produce aldehydes, wherein the catalyst composition comprises a rhodium source and a tetradentate ligand, said tetradentate ligand comprising the following structure:

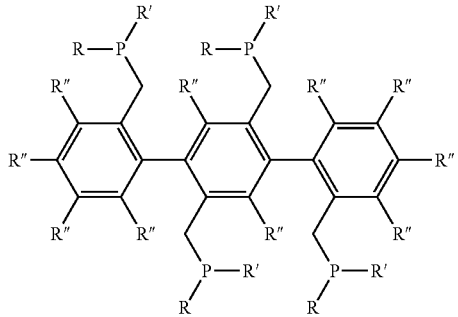

R=aryl, arylalkyl, alkyl-substituted-aryl, hydrocarbyl alkyl, R optionally being substituted with heteroatom and other functional groups;
R'=aryl, arylalkyl, alkyl-substituted-aryl, hydrocarbyl alkyl, R' optionally being substituted with heteroatom and other functional groups;
R"=H, aryl, tertiary-butyl and heteroatom and other functional groups;
Heteroatom and other functional groups=F, thioethers, aryl or alkyl ethers, esters bound through the single oxygen bond, CF3, carboxylic acid esters, carboxylic amides and alkali metal salts of sulfonic acid;
P=Phosphorus Atom.

2. A process according to claim 1, wherein the aldehydes are produced in an N:I ratio of from about 15:1 up to about 100:1.

3. The process according to claim 1, wherein the olefin is an unsubstituted linear alpha-olefin.

4. The process according to claim 3, wherein the olefin is propylene, 1-butene, 1-pentene, 1-hexene, 1-heptene, 1-octene, 1-nonene, 1-decene, 1-undecene, 1-dodecene or mixtures thereof.

5. The process according to claim 1, wherein the olefin is bicyclic olefin 2-vinyl-bicyclo[2.2.1]-heptane, vinylcyclohexane, vinylcyclopentane, 1,8-octadiene, cis-butene-2, trans-butene-1, cis-octene-2, trans-octene-2 or allyl alcohol.

6. The process of claim 1, wherein reaction temperature ranges from about 25 degrees Celsius up to about 140 degrees Celsius.

7. The process of claim 6, wherein reaction temperature ranges from about 80 degrees Celsius up to about 125 degrees Celsius.

8. The process of claim 7, wherein reaction temperature ranges from about 90 degrees Celsius up to about 110 degrees Celsius.

9. The process of claim 1, wherein reaction pressure ranges from about 14.7 psig up to about 500 psig.

10. The process of claim 9, wherein reaction pressure ranges from about 100 psig up to about 300 psig.

11. The process according to claim 1, wherein a mole ratio of olefin fed per hour to rhodium precursor present in a reactor is from about 1,000,000:1 to about 1000:1.

12. The process according to claim 11, wherein the mole ratio of olefin fed per hour to rhodium precursor present in the reactor is from about 300,000:1 to about 50,000:1.

13. The process according to claim 1, wherein the mole ratio of olefin to rhodium precursor present in a reactor is from about 10,000:1 to about 100:1.

14. The process according to claim 13, wherein the mole ratio of olefin to rhodium precursor in the reactor is from about 10,000:1 to about 2000:1.

15. The process of claim 1, wherein the mole ratio of the tetradentate ligand to the rhodium source ranges from about 50:1 down to about 1:1.

16. The process of claim 15, wherein the mole ratio of the tetradentate ligand to rhodium source ranges from about 15:1 down to about 2:1.

17. The process of claim 16, wherein the mole ratio of the tetradentate ligand to rhodium source ranges from about 12:1 down to about 3:1.

18. A catalyst composition comprising a rhodium source and a tetradentate ligand comprising the following structure:

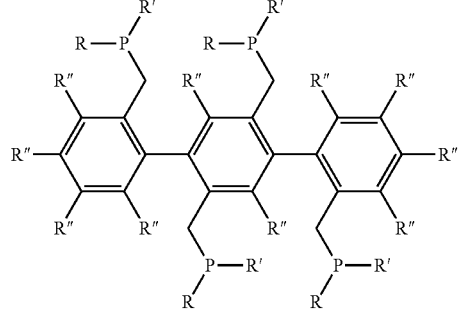

R=aryl, arylalkyl, alkyl-substituted-aryl, hydrocarbyl alkyl, R optionally being substituted with heteroatom and other functional groups;
R'=aryl, arylalkyl, alkyl-substituted-aryl, hydrocarbyl alkyl, R' optionally being substituted with heteroatom and other functional groups;
R"=H, aryl, tertiary-butyl and heteroatom and other functional groups;
Heteroatom and other functional groups=F, thioethers, aryl or alkyl ethers, esters bound through the single oxygen bond, CF3, carboxylic acid esters, carboxylic amides and alkali metal salts of sulfonic acid;
P=Phosphorus Atom.

19. A tetradentate ligand adapted for use with a catalyst composition, the tetradentate ligand comprising the following structure:

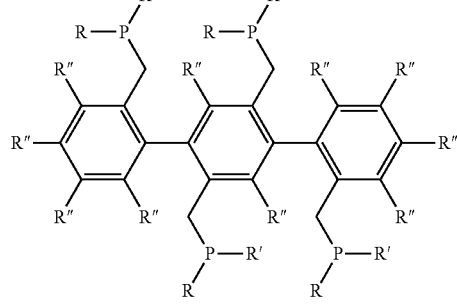

R=Phenyl
R'=Phenyl
R"=H
P=Phosphorus Atom.

* * * * *